(12) United States Patent
Leifer et al.

(10) Patent No.: US 10,720,235 B2
(45) Date of Patent: Jul. 21, 2020

(54) METHOD AND SYSTEM FOR PREFERENCE-DRIVEN FOOD PERSONALIZATION

(71) Applicant: Kraft Foods Group Brands LLC, Chicago, IL (US)

(72) Inventors: Tjarko Leifer, San Francisco, CA (US); Erik Andrejko, San Francisco, CA (US); Sivan Aldor-Noiman, San Francisco, CA (US)

(73) Assignee: KRAFT FOODS GROUP BRANDS LLC, Chicago, IL (US)

( * ) Notice: Subject to any disclaimer, the term of this patent is extended or adjusted under 35 U.S.C. 154(b) by 0 days.

(21) Appl. No.: 16/258,426

(22) Filed: Jan. 25, 2019

(65) Prior Publication Data

US 2019/0228856 A1    Jul. 25, 2019

Related U.S. Application Data

(60) Provisional application No. 62/621,785, filed on Jan. 25, 2018.

(51) Int. Cl.
*G06Q 30/00* (2012.01)
*G16H 20/60* (2018.01)
(Continued)

(52) U.S. Cl.
CPC ......... *G16H 20/60* (2018.01); *G06F 16/9035* (2019.01); *G06F 16/90324* (2019.01);
(Continued)

(58) Field of Classification Search
CPC .................................................... G06Q 30/00
See application file for complete search history.

(56) References Cited

U.S. PATENT DOCUMENTS

| 5,212,766 A * | 5/1993 | Arima | G06N 3/063 |
| | | | 706/25 |
| 6,370,513 B1 * | 4/2002 | Kolawa | G06Q 30/02 |
| | | | 705/15 |

(Continued)

FOREIGN PATENT DOCUMENTS

WO    2018198100 A1    11/2018

OTHER PUBLICATIONS

Innit1, Web.archive.org/web/20180107231742/https://www.innit.com, dated Jan. 7, 2018. (Year: 2018).*

(Continued)

*Primary Examiner* — Mark A Fadok
(74) *Attorney, Agent, or Firm* — Jeffrey Schox

(57) ABSTRACT

A method for improving food-related personalized for a user including determining food-related preferences associated with a plurality of users to generate a user food preferences database; collecting dietary inputs from a subject matter expert (SME) at an SME interface associated with the user food preferences database; determining personalized food parameters for the user based on the user food-related preferences and the dietary inputs; receiving feedback associated with the personalized food parameters from the user; and updating the user food preferences database based on the feedback.

13 Claims, 2 Drawing Sheets

(51) Int. Cl.
    *G06F 16/9032* (2019.01)
    *G06F 16/9035* (2019.01)
    *G16H 10/60* (2018.01)
    *G06N 3/08* (2006.01)
    *G06N 20/10* (2019.01)
    *G06N 5/04* (2006.01)

(52) U.S. Cl.
    CPC .............. *G06N 3/08* (2013.01); *G06N 5/04* (2013.01); *G06N 20/10* (2019.01); *G16H 10/60* (2018.01)

(56) References Cited

U.S. PATENT DOCUMENTS

| | | | |
|---|---|---|---|
| 8,276,505 B2* | 10/2012 | Buehler | A23L 5/10 99/326 |
| 8,429,026 B1* | 4/2013 | Kolawa | G06Q 30/00 705/26.7 |
| 8,849,805 B2 | 9/2014 | Osaki | |
| 9,212,996 B2* | 12/2015 | Watson | G01N 21/31 |
| 2008/0086374 A1* | 4/2008 | Aitken | G06F 19/3475 705/14.27 |
| 2009/0037288 A1 | 2/2009 | Christensen | |
| 2009/0075242 A1 | 3/2009 | Schwarzberg et al. | |
| 2009/0236333 A1* | 9/2009 | Ben-Shmuel | H05B 6/6402 219/702 |
| 2009/0254541 A1* | 10/2009 | Kolawa | G06Q 10/063 |
| 2013/0224694 A1 | 8/2013 | Moore et al. | |
| 2013/0269297 A1 | 10/2013 | Minvielle | |
| 2013/0280681 A1 | 10/2013 | Narayan et al. | |
| 2014/0052722 A1 | 2/2014 | Bertsimas et al. | |
| 2015/0066909 A1 | 3/2015 | Uchida et al. | |
| 2015/0287056 A1* | 10/2015 | Osogami | G06F 17/16 705/7.29 |
| 2015/0290795 A1* | 10/2015 | Oleynik | G05B 19/42 700/257 |
| 2016/0081515 A1* | 3/2016 | Aboujassoum | A47J 36/00 426/231 |
| 2016/0180739 A1* | 6/2016 | Minvielle | G09B 19/06 434/127 |
| 2016/0275397 A1* | 9/2016 | Neil | G06N 3/0472 |
| 2016/0350834 A1* | 12/2016 | Wilson | G06N 3/084 |
| 2017/0053551 A1 | 2/2017 | Prisk | |
| 2017/0320655 A1* | 11/2017 | Minvielle | B65D 85/00 |
| 2017/0372197 A1* | 12/2017 | Baughman | G06N 3/0635 |
| 2018/0033074 A1* | 2/2018 | Grueneberg | G06Q 30/0633 |
| 2018/0137249 A1* | 5/2018 | Eggebraaten | G16H 50/70 |
| 2018/0203978 A1* | 7/2018 | Basu | G16H 50/30 |
| 2018/0308143 A1* | 10/2018 | Chan | G06Q 30/06 |
| 2018/0314804 A1* | 11/2018 | Gorre | G06F 19/3475 |
| 2019/0050624 A1* | 2/2019 | Chai | G06K 9/0053 |
| 2019/0073581 A1* | 3/2019 | Chen | G06Q 50/01 |
| 2019/0147340 A1* | 5/2019 | Zhang | G06N 3/084 706/25 |
| 2019/0228855 A1* | 7/2019 | Leifer | G16H 20/60 |
| 2019/0228856 A1* | 7/2019 | Leifer | G16H 20/60 |

OTHER PUBLICATIONS

Innit2, "Innit unveils connected food platform", Businesswire, dataed May 16, 2016. (Year: 2016).*

Innit3, Bojinov, Hristo, "Deep Learning in the connected kitchen or "Launching a computer vision program in a new vertical"", dated Jun. 8, 2017 (Year: 2017).*

Innit, Kontzer, "How deep learning will stir more joy into your cooking", Nvidia, dated May 11, 2017 (Year: 2017).*

INNIT5, "Innit launches app to revolutionize the way we eat", Innit Press Release, dated Dec. 5, 2017. (Year: 2017).*

Innit6, Evangelista, Benny, SF startup's recipe for smart kitchen starts with oven, San Francisco Cronicle, dated Sep. 4, 2016 (Year: 2016).*

Innit7, Judkis, "Recipies are dead: what the future of cooking might look like,", dated Dec. 6, 2017. (Year: 2017).*

* cited by examiner

METHOD AND SYSTEM FOR PREFERENCE-DRIVEN FOOD PERSONALIZATION

CROSS REFERENCE TO RELATED APPLICATIONS

This application claims the benefit of U.S. Provisional Application Ser. No. 62/621,785, filed 25 Jan. 2018, which is incorporated herein in its entirety by this reference.

TECHNICAL FIELD

This invention relates generally to the food technology field, and more specifically to a new and useful method and system for improving food-related personalization.

BACKGROUND

In the food technology field, the typical food consumer or preparer is often an amateur that lacks specialized knowledge in food science, recipe creation, and related aspects of food technology. Thus recipes, including a set of ingredients and guidelines for food preparation, are created by more experienced food preparers for dissemination to amateur food preparers and/or the public at large. Amateur food preparers can attempt to seek out detailed recipe information that meets their food preferences, but the information is often inconsistent across available sources (e.g., the Internet) and performing such a search requires some preexisting specialized knowledge concerning what to seek out. Consulting with a subject matter expert (SME) can be helpful, but one-on-one recommendations are necessarily bespoke and thus scale poorly to the need for domain knowledge across the population of amateur food prepares; conventional approaches fail to suitably generalize SME knowledge across a population of amateur food preparers that require such information.

Thus, there is a need in the food technology field for methods and systems for improving food-related personalization to user needs. This invention provides such new and useful methods and systems.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

Figure 1:
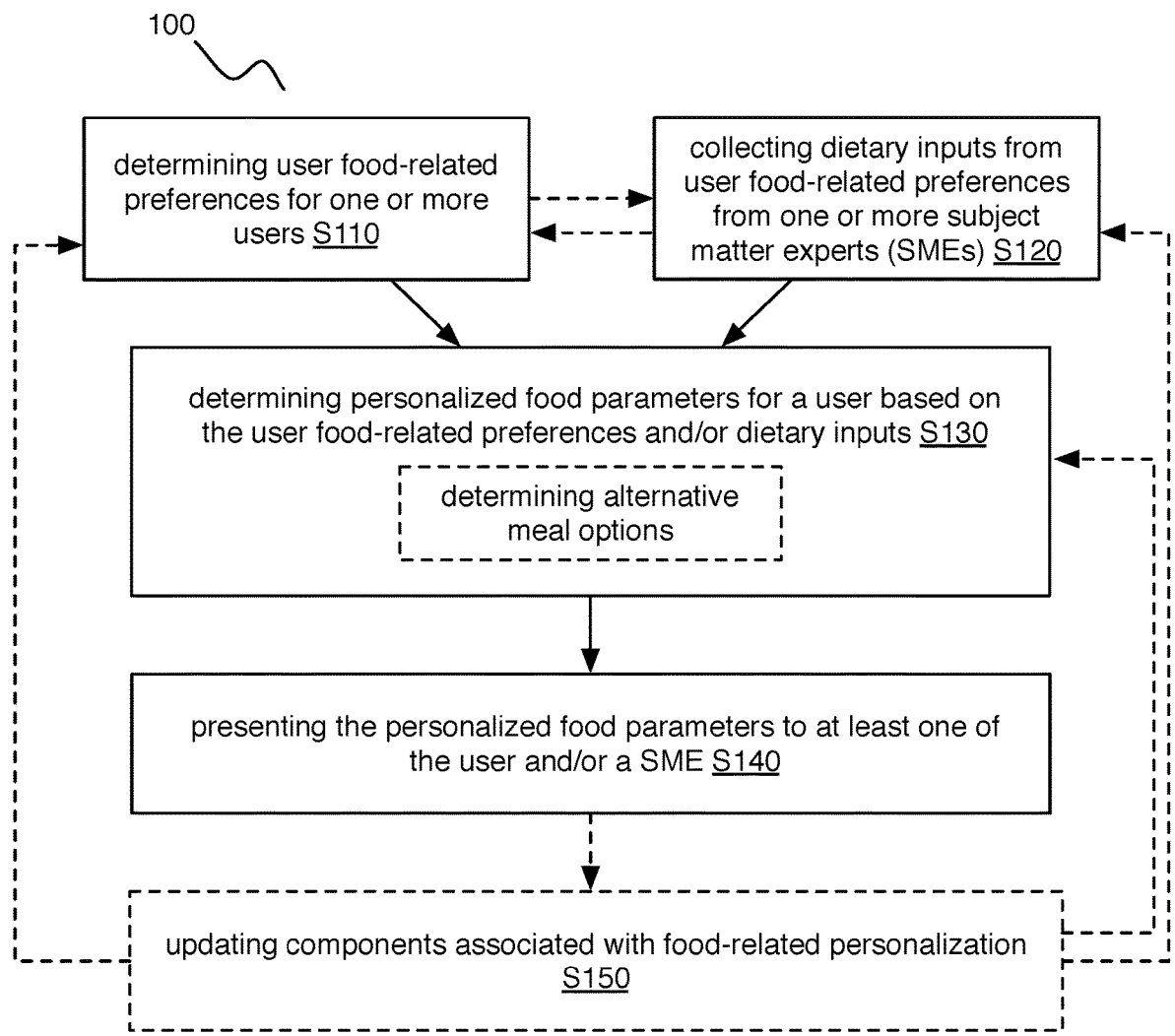
FIG. 1 is a schematic representation of variations of embodiments of the method.
Figure 2:
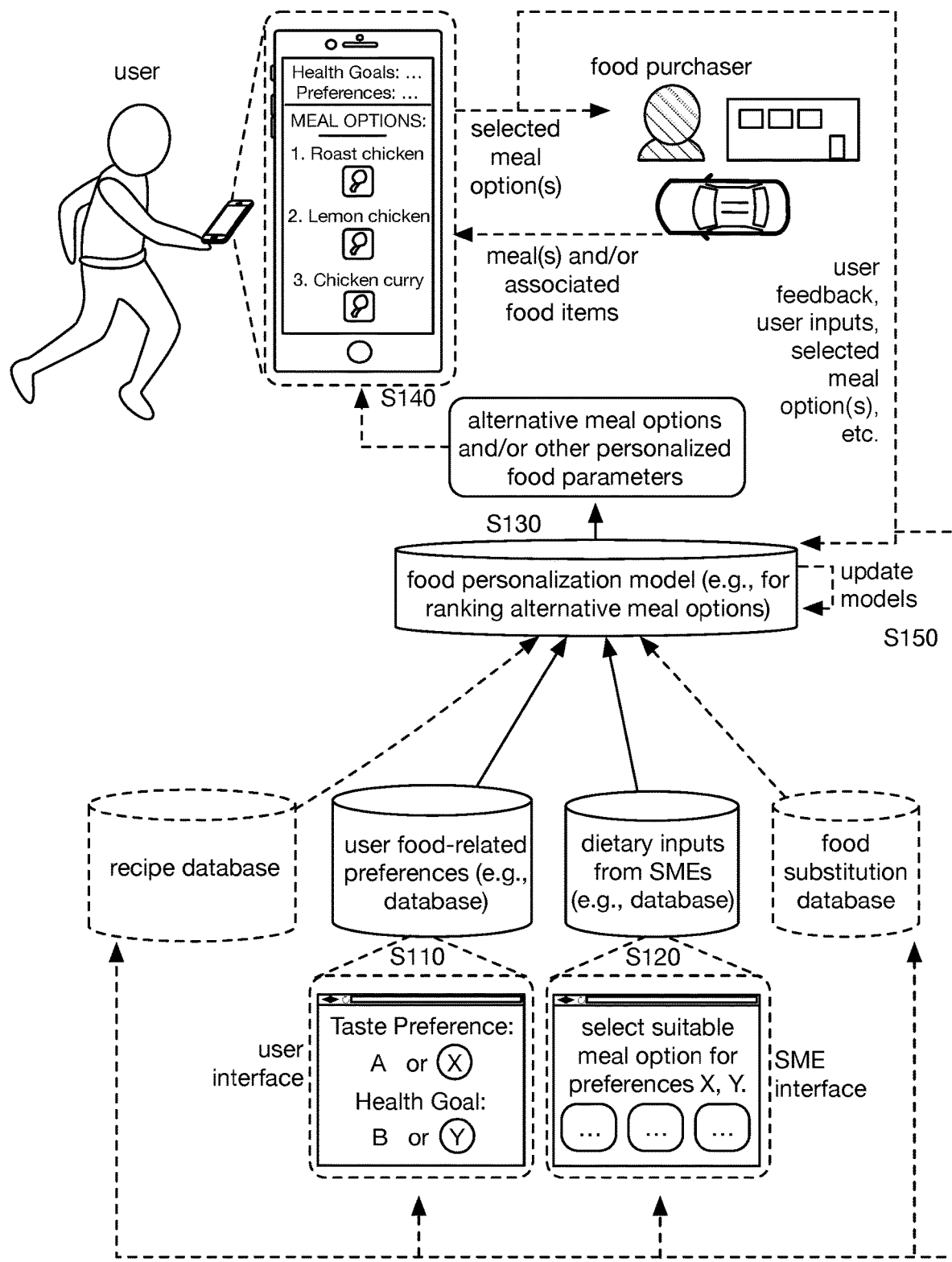
FIG. 2 is a schematic representation of variations of embodiments of the method.

As shown in FIGS. 1-2, embodiments of a method 100 for improving food-related personalized for a user can include: determining user food-related preferences (e.g., health goals, taste preferences, dietary restrictions, etc.) associated with one or more users S110; collecting one or more dietary inputs (e.g., selections of meal options suitable for satisfying different food-related preferences; etc.) from one or more subject matter experts (SMEs) and/or other entities (e.g., human entities, non-human entities, entities associated with machine learning techniques and/or other computational processing methods, etc.) associated with the food-related personalization S120; determining personalized food parameters (e.g., personalize alternative meal options accommodating the user food-related preferences, etc.) for the user based on the user food-related preferences and the dietary inputs S130; and/or presenting the personalized food parameters to at least one of the user and a subject matter expert S140.

Additionally or alternatively, embodiments of the method 100 can include: updating a food personalization model, other components associated with determining personalized food parameters, and/or any other suitable components associated with the method 100, S150.

Embodiments of the method 100 and/or the system 200 can function to leverage user food-related preferences, other user inputs (e.g., user selections of meals from a presented ranked list of meal alternatives; etc.), SME inputs (e.g., dietary inputs associated with meal alternatives for a user profile, etc.), and/or other suitable inputs associated with food-related personalization for determining personalized meal alternatives (e.g., alternative meal options, etc.) and/or other suitable food parameters that can be presented to and/or selected by one or more users (e.g., where a personalized meal option selected by a user can be fulfilled, such as through purchasing and/or delivery to the user, etc.). Additionally or alternatively, embodiments can function to establish a scalable food personalization system leveraging SME expertise to improve and apply food personalization digital processes to a plurality of users. However, embodiments can have any suitable functionality.

Additionally or alternatively, data described herein can be associated with any suitable temporal indicators (e.g., seconds, minutes, hours, days, weeks, etc.) including one or more: temporal indicators indicating when the data was collected (e.g., when a dietary input was inputted by an SME at an SME interface, etc.), determined (e.g., timestamps associated with determination of a ranked list of personalized meal options, etc.), transmitted, received (e.g., when a user selection of a personalized meal option was received), and/or otherwise processed; temporal indicators providing context to content described by the data; changes in temporal indicators (e.g., data over time; change in data; data patterns; data trends; data extrapolation and/or other prediction; etc.); and/or any other suitable indicators related to time.

Additionally or alternatively, parameters, metrics, inputs, outputs, and/or other suitable data can be associated with value types including: scores (e.g., meal suitability scores upon which a ranked list of personalized meal options can be based; substitutability scores for ingredient substitution, such as for recipe modification; user food preference scores indicating a strength of the preference by the user; similarity scores between types of ingredient entities; recipe matching scores indicating the degree to which user food-related preferences are satisfied by a given recipe, such as influenced by dietary inputs from SMEs; etc.), binary values (e.g., dietary inputs indicating that a personalized meal option satisfies or does not satisfy a set of user food-related preferences, etc.), classifications (e.g., meal types, SME types, user types, user food-related preference types, ingredient entity types, etc.), confidence levels (e.g., associated with meal suitability scores, rankings, dietary inputs, etc.), values along a spectrum, and/or any other suitable types of values. Any suitable types of data described herein can be used as inputs (e.g., for different models described herein; for portions of the method 100; etc.), generated as outputs (e.g., of models), and/or manipulated in any suitable manner for any suitable components associated with the method 100 and/or system 200.

One or more instances and/or portions of the method 100 and/or processes described herein can be performed asynchronously (e.g., sequentially, such as through feedback loops including determining personalized food parameters for a user with a food personalization model, collecting user inputs and/or other suitable inputs associated with the presented personalized food parameters, and updating the food personalization model based on the inputs associated with the personalized food parameters, etc.), concurrently (e.g., in parallel; concurrently on different threads for parallel computing to improve system processing ability for improving food-related personalization across a plurality of users, user food-related preferences, SMEs, etc.), in temporal relation to a trigger event (e.g., performance of a portion of the method 100), and/or in any other suitable order at any suitable time and frequency by and/or using one or more instances of the system 200, components, and/or entities described herein.

Embodiments of the system 200 can include a food personalization system (e.g., a remote computing system configured to improve food-related personalization; etc.), databases (e.g., user database, SME database, meal database, recipe database, food substitution database, etc.), and/or any other suitable components. Additionally or alternatively, the system 200 and/or portions of the system 200 can entirely or partially be executed by, hosted on, communicate with, and/or otherwise include: a remote computing system (e.g., a server; at least one networked computing system; stateless; stateful; etc.), a local computing system, a user device (e.g., a computing device operable to present a user interface and/or SME interface; a cooking device such as a smart cooking device operable to receive control instructions for cooking a selected personalized meal option determined by portions of the method 100; a medical device such as a wearable health tracker; other supplementary devices operable to collect data indicative of progress towards health goals, such as progress associated with consumption of personalized meal options; etc.), and/or any suitable component. Communication by and/or between any components of the system 200 can include wireless communication (e.g., WiFi, Bluetooth, radiofrequency, etc.), wired communication, and/or any other suitable types of communication.

The components of the system 200 can be physically and/or logically integrated in any manner (e.g., with any suitable distributions of functionality across the components in relation to portions of the method 100; etc.). However, the method 100 and/or system 200 can be configured in any suitable manner.

In relation to food-related data, the method 100 can include representation of any suitable data as a vector. Vector representations of food-related data (e.g., recipe data structures, ingredients or ingredient entities, user food preferences, etc.) can function to enable comparison of such data (e.g., with like data, with similar data, with subsets of partially similar data, etc.) across a vector of data features. Vector representations can also function to enable representation of food-related data at various hierarchies (e.g., wherein a recipe can be represented by a recipe vector and define a set of ingredients that are each represented by an ingredient vector).

Vector representations of food related data can enable constraints to be applied in the vector space in which the food-related data is represented. For example, in determining personalized food parameters (e.g., in accordance with one or more variations of Block S130), recipe vector representations can be compared to the constraints (e.g., elementwise constraints on the magnitude of components of the vector, norm-based constraints on the combined vector magnitude of the vector representation, dietary constraints determined by an SME, etc.) to determine whether the recipe represented by the recipe vector satisfies the constraints of the personalized food plan. However, vector representations can be otherwise suitably used to make any other suitable comparison.

Vector representations of food-related data are preferably generated as a result of processing the food-related data at a trained synthetic neural network defining a plurality of neuronal layers. Such neural networks can be convolutional neural networks (CNNs), deep learning networks, and any other suitable configuration or representation of a linked set of numerical operations that process input data into output data in a vectorized manner. The vector representation of a food-related datum is preferably an intermediate layer of such a neural network, and thus represented by a set of weights (e.g., vector component values) defining a vector in a vector space spanning the domain of the neural network. However, vector representations of food-related data can be otherwise suitably generated.

2.1 Determining User Food-Related Preferences

Block S110 can include determining user food-related preferences associated one or more users, which can function to improve food-related personalization (e.g., determination of personalized meal options; other portions of the method 100) for a user according to associated preferences. User food-related preferences can include any one or more of: goals (e.g., health goals such as meeting specific health metrics; diet goals such as maintaining a specific diet; weight goals; fitness goals; nutrition goals such as being below a daily caloric threshold; aesthetic goals; sustainability goals; environmental impact goals; financial goals such as meeting a financial budget for food-related costs; cooking goals such as improving cooking skills; etc.), dietary preferences (e.g., vegan, keto, gluten-free, allergies, caloric preferences, macronutrient preferences, micronutrient preferences, etc.), taste preferences (e.g., types of cuisines, texture, types of tastes, preferences for sweetness, sourness, saltiness, bitterness, umami, etc.), cooking preferences (e.g., time to cook, difficulty, user skill level for cooking, serving size, cooking devices and/or other suitable tools involved, etc.), grocery item preferences (e.g., organic versus non-organic, brands, current food items already owned by the user, etc.), and/or any other suitable food-related preferences. User food-related preferences (e.g., goals, etc.) can be in any suitable form (e.g., inputted by a user in a suitable form; outputted by an inference model in a suitable form; etc.) including any one or more of: natural language (e.g., "I want to lose weight" as a weight goal, etc.), scores (e.g., below a daily caloric intake of 2000 calories, etc.), binary values (e.g., gluten free or not gluten free, etc.), and/or any suitable value type.

User food-related preferences can be determined and/or applied at a recipe and/or meal granularity level (e.g., whether a recipe and/or meal satisfies a set of user health goals; comparing taste preference to a "fettuccini alfredo" meal, etc.), a food item and/or recipe item level (e.g., comparing nutrition goals such as a carbohydrate intake goals to carbohydrate content to specific food items such as different types of bread, etc.), a food plan level (e.g., applying user food-related preferences to a personalized food plan including a plurality of alternative meal options, etc.). In a variation, different types of user food-related preferences can be applied with different weightings in determining outputs associated with other portions of the method 100 (e.g., determining personalized food parameters, etc.), such as weighting (e.g., ranking) health goals as a priority over taste preferences (e.g., in ranking alternative meal options from a plurality of potential meal options), where the weightings can be predetermined, user-selected, automatically adjusted (e.g., based on user interactions at a user interface presented at an application executing on the user's computing device; etc.), and/or otherwise determined. However, any suitable user food-related preferences can be applied in any suitable manner (e.g., with any suitable weighting) for determining any suitable food parameters and/or other outputs associated with the method 100.

Determining user food-related preferences is preferably based on user inputs. For example, Block S110 can include collecting user selections for different potential user food-related preferences presented to a user at an interface (e.g., web interface, mobile application interface, etc.). In another example, Block S130 can include inferring user food-related preferences based on user actions (e.g., user selections of meal options; user clicks, touch gestures, viewing behavior, other activity behavior, etc.), user feedback (e.g., collected in response to presenting a prompt for user feedback regarding alternative meal options, etc.), and/or other suitable user inputs. In another example, Block S130 can include extracting user food-related preferences from third party databases (e.g., medical history databases, grocer databases, food delivery services databases, social media databases, health application databases, etc.). In a specific example, Block S110 can include applying natural language processing to medical records associated with a user to extract health-related goals (e.g., inferred from the medical records; recommended by a health professional; etc.). In another specific example, Block S110 can include querying an API of a third-party health application to retrieve health-related metrics (e.g., heart rate, blood pressure, physical activity levels, etc.) describing the health of the user; and determining health-related goals (e.g., improving cardiovascular metrics, etc.) based on the health-related metrics. In another example, Block S130 can include inferring user food-related preferences based on food device data (e.g., identifying dietary habits inconsistent with health goals based on classification data describing recent food items cooked by a connected food device for the user, etc.). In another example, Block S130 can include inferring user food-related preferences based on data received, sampled, and/or otherwise suitably collected from social media accounts (e.g., Instagram™, Facebook™, Yelp™) based on information posted by the user and/or others associated with (e.g., in the network of) the user, user check-ins at an establishment associated with food, etc. In another example, Block S130 can include inferring user food-related preferences based on user characteristics (e.g., demographic information, geographic location, user interests, user affiliations, etc.). Additionally or alternatively, user food-related preferences can be determined with a user food preference model (e.g., a machine learning model, etc.) and/or other suitable approach (e.g., described herein) based on any suitable types of data.

In a variation, determining user food-related preferences can include generating a user food preferences database (e.g., associating user food-related preferences with user identifiers such as user account handles; assigning user profiles to SMEs for evaluation in relation to mapping user food-related preferences to suitable food parameters such as meal options; associating suitable recipe item substitutions for satisfying different types of user food-related preferences, etc.). However, determining user food-related preferences can be performed in any suitable manner. In variations, the method can include deriving a recipe vector representation based on the user food preferences database, including: training a neural network model using the food preferences as inputs, wherein the neural network model is made up of a plurality of neuronal layers, and wherein the recipe vector representation is generated from (e.g., equivalent to) an intermediate layer (e.g., the weights associated with the intermediate layer) of the plurality of neuronal layers. Analogously, the method can include deriving a vector representation of any other suitable type of food-related data (e.g., ingredients, preparation parameters, user food preferences, etc.) described herein in a similar manner (e.g., using a different neural network model configured similarly but directed to solving a distinct problem, wherein the distinct problem is related to the food-related data type being represented; using an end-to-end model encompassing each suitable food-related data type, where a subset of the dimensions of the model correspond to a particular food-related data type; etc.). However, the food preferences database can be otherwise suitably generated.

2.2 Collecting Dietary Inputs

Block S120 recites: collecting one or more dietary inputs from one or more SMEs associated with the food-related personalization, which can function to collect expert-provided data for guiding automated determination (e.g., through providing training data for machine learning models; through generating a series of computer-implemented rules that can be generalized to subgroups of users based on shared user food-related preferences; etc.) of personalized food parameters for users in accordance with corresponding user food-related preferences.

Dietary inputs can include any one or more of: selections (e.g., selection of a meal option from a plurality of alternative meal options presented in relation to prompting a SME to select the meal that best satisfies one or more user food-related preference types and/or other suitable criteria; matching meal options and/or other suitable food parameters to users, user food-related preferences, user demographics, other suitable user characteristics, and/or other suitable components, etc.), natural language (e.g., "suitable for gluten-free diets", "satisfies low caloric intake diets", "unsuitable for users with high blood pressure", etc.), scores (e.g., a score from 1 to 10 for a meal option satisfying one or more user goals and/or other suitable user food-related preferences, etc.), rankings (e.g., ranked meal options for satisfying one or more user food-related preferences, etc.), recipe-related data structures (e.g., selection of recipe items suitable for substitution into recipes, such as to accommodate one or more user food-related preferences, etc.), forms analogous to user food-related preferences, and/or any other suitable types of inputs informing food-related personalization.

Dietary inputs can be collected for, inputted for, and/or otherwise associated with (e.g., at a food personalization database) one or more of: a recipe and/or meal granularity level (e.g., selecting recipes corresponding to recipe data structures associated with nutrient information satisfying user nutrition goals, etc.), a food item and/or recipe item level (e.g., identifying recipe item substitutions that can be made to accommodate a low carbohydrate diet while maintaining a comparable taste profile, etc.), a food plan level (e.g., a selection from different food plan templates as suitable for one or more user food-related preferences; SME-generated menu of alternative meal options selected for satisfying user health goals and/or other suitable user food-related preferences; etc.), one or more users (e.g., receiving a personalized food plan selection from a SME for one or more users), one or more user profile types (e.g., for a user subgroup sharing one or more user characteristics such as user food-related preferences, etc.), one or more user food-related preferences (e.g., for specific sets of user food-related preferences such as for specific combinations of health goals and taste preferences, etc.) and/or for any other suitable components at any suitable granularity level.

SMEs can include any one or more of: a nutritionist, dietician, personal trainer, other fitness professional, health coach, healthcare professional, physician, culinary professional, and/or any other suitable individual with food-related (e.g., health-related, etc.) expertise.

Dietary inputs are preferably collected through an SME interface (e.g., web interface, mobile application interface). For example, a series of sets of alternative meal options (e.g., grouped by meal type, food item type, recipe type, nutrition characteristics, preparation requirements, cost, other food-related characteristics) can be presented to an SME at an SME interface, where the interface can prompt the SME to select one or more meal options (e.g., ranking meal options) from a set of alternative meal options based on suitability for one or more user food-related preferences (e.g., prompting the SME to select the meals that satisfy a specific set of nutrition goals, dietary preferences, and taste preferences, etc.). In another example, Block S120 can include presenting a recipe (e.g., ingredient entities for a recipe), potential food substitutions (e.g., provided by a food substitution model; a ranked ordered list of substitutions), a set of user food-related preferences, and a prompt to identify food substitutions satisfying the set of user food-related preferences. Food-related components presented to SMEs can be in one or more forms including: textual (e.g., recipe descriptions, taste profile descriptions, etc.), graphical (e.g., images, video, augmented reality, virtual reality, associated with a meal, food items, preparation, etc.), audio (e.g., recipe preparation instructions, etc.), and/or any other suitable forms. In another example, Block S120 can include presenting user analytics (e.g., analyzed user behaviors; historic user inputs such as historic user selections of meal options such as for a user subgroup sharing one or more user food-related preferences, etc.), additional food-related information describing meal options and/or other food parameters, and/or any other suitable information suitable for guiding and/or otherwise facilitating dietary inputs from SMEs.

Additionally or alternatively, dietary inputs can be inferred and/or otherwise obtained. In variations, dietary inputs can be collected from one or more of: communications involving an SME (e.g., messages between an SME and a user, where natural language processing and/or other suitable approaches can be applied in analyzing the message content to infer dietary inputs; messages between SMEs, such as discussions regarding meal options and/or user food-related preferences; etc.), third party databases (e.g., online health-related forums such as fitness activity forums; food-related databases including nutrition information; medical databases; etc.), other dietary inputs (e.g., determining a subgroup of meal options sharing one or more food-related characteristics, collecting a dietary input selecting a meal option from the subgroup as satisfying one or more user food-related preferences, and generalizing the selection of the meal option to the other meal options in the subgroup as satisfying the one or more user food-related preferences; performing other suitable generalization, extrapolation, and/or other suitable scaling operations for leveraging one or more dietary inputs to apply to a larger set of meal options and/or other food parameters, etc.), social media accounts associated with the user (e.g., as described above), and/or through any other suitable components. However, collecting dietary inputs associated with SMEs can be performed in any suitable manner.

2.3 Determining Personalized Food Parameters

Block S130 recites: determining personalized food parameters based on the user food-related preferences and the dietary inputs, which can function to leverage SME expertise (e.g., implemented within a food personalization model, etc.) to determine meal options and/or other suitable food parameters personalized to the preferences of one or more users. In a variation, personalized food parameters (e.g., meal option data structures, recipe data structures, etc.) can be stored (e.g., at a remote computing system) in association with food-related preferences (e.g., to facilitate mapping of food-related preferences to suitable personalized food parameters satisfying the food-related preferences, etc.), user identifiers (e.g., user accounts for which the personalized food parameters were determined, etc.), SME identifiers (e.g., metadata indicating sources of dietary inputs associated with the personalized food parameters, etc.), and/or any other suitable data.

Personalized food parameters can include any one or more of: meal options (e.g., where different options correspond to different types of meals; where a meal option corresponds to recipe; modified meal options with one or more item substitutions; etc.), pre-selected food options (e.g., an automatically selected meal option to be fulfilled absent user input, etc.), recipes, modified recipes (e.g., recipes with one or more recipe item modifications, preparation instructions modifications, taste profile modifications, any other suitable food-related characteristic modifications, etc.), recommendations (e.g., different meal options meeting different user food-related preferences; health recommendations such as dietary behavior recommendations, physical activity recommendations; etc.), recipe modifications, food purchase plans (e.g., a list of grocery items to purchase, where the grocery items can correspond to ingredients included in a recommended recipe, etc.), goal-related analytics (e.g., analytics regarding effect of alternative meal options in meeting user food-related goals such as nutrition goals, etc.), historic food parameters (e.g., for comparison with current food parameters; for maintaining trends associated with achieving user food-related goals; etc.), food-related device parameters (e.g., control instructions for controlling a cooking device to cook a personalized meal based on a recommended meal option and/or other suitable food parameters, where the control instructions can be transmitted to the cooking device, etc.), and/or any other suitable food parameters (e.g., associated with providing food-related personalization across a plurality of different users to improve tailored delivery of food items, of food-related content, etc.).

For example, Block S130 can include determining, for a user, a ranked list of alternative meal options (e.g., combinations of different recipes, combinations of different modifications of a recipe, etc.) based on user food-related preferences (e.g., health goals, dietary restriction preferences, taste preferences, etc.) and dietary inputs from SMEs (e.g., indicating suitable meal options, food plans, and/or other suitable food parameters for accommodating the user food-related preferences; etc.). In another example, Block S130 can include determining a base meal option (e.g., corresponding to a base recipe) for a user (e.g., satisfying a subset of the user food-related preferences; etc.); and determining a modified meal option (e.g., better suited for achieving user food-related goals; meeting other user food-related preferences; with recipe item substitutions applied to the base recipe, such as based on ranked food substitutability outputs from a food substitution model; satisfying all of the user food-related preferences; associated with a calculated higher probability of meeting user food-related preferences; etc.) based on the base meal option and dietary inputs (and/or other suitable data). However, any suitable number of intermediary processes can be performed in any suitable order to generate personalized food parameters.

Determining personalized food parameters is preferably based on user food-related preferences and/or dietary inputs, but can additionally or alternatively be based on food substitution parameters, fulfillment parameters (e.g., describing purchase fulfillment capabilities, food delivery capabilities, etc.), and/or any other suitable data. In an example, Block S130 can include determining personalized food parameters to satisfy user food-related preferences (e.g., selecting meal options satisfying a fat macronutrient restriction, such as satisfying a daily restriction amount, a weekly restriction amount, and/or along any suitable time scale, where any suitable personalized food parameters can accommodate user food-related preferences along any suitable time scale; ranking meal options based on cost preferences; etc.). In another example, determining personalized food parameters can be based on dietary inputs from SMEs indicating whether and/or to what degree a food parameters (e.g., a meal option) will improve results associated with user food-related goals (e.g., health goals) and/or other suitable user food-related preferences.

Block S130 and/or other suitable portions of the method 100 can include determining and/or applying one or more food-related models (e.g., food personalization models for determining food parameters; dietary input models for determining dietary inputs; food preference models for determining user food-related preferences; etc.) and/or other approaches, where the models and/or other approaches can include any one or more of: probabilistic properties, heuristic properties, deterministic properties, and/or any other suitable properties. In variations, Block S130 and/or other suitable portions of the method 100 can employ machine learning approaches (e.g., for the food personalization models, etc.) including any one or more of: semi-supervised learning, supervised learning (e.g., using logistic regression, using back propagation neural networks, using random forests, decision trees, etc.), unsupervised learning (e.g., using an Apriori algorithm, using K-means clustering), reinforcement learning (e.g., using a Q-learning algorithm, using temporal difference learning), a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial least squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and/or any suitable form of machine learning algorithm.

In a specific example, Block S110 can include applying a deep neural network with dietary inputs, user food-related preferences, and/or other suitable data as inputs to determine personalized food parameters. The models (and/or portions of the method 100) and/or other approaches can be universally applicable (e.g., the same models across users, food-related preference types, SMEs, locations, etc.), specific to different entities and/or combinations of entities (e.g., different models for different subgroups of users sharing one or more user food-related preferences and/or other suitable characteristics, for different food groupings such as meal option groupings by food characteristics; etc.), specific to different geographic regions, and/or can be applicable in any suitable manner.

Each model can be run, validated, verified, reinforced, calibrated, and/or updated: once; at a predetermined frequency (e.g., at a dinner time manually selected or inferred for a user; etc.); every time an instance of an embodiment and/or portion of the method 100 is performed, every time a trigger condition is satisfied (e.g., a user selects an option at a mobile application to browse meal options; a user logging in; collecting updated dietary inputs and/or other suitable data; etc.), and/or at any other suitable time and frequency. Models can be run or updated concurrently with one or more other models, serially, at varying frequencies, and/or at any other suitable time. Each model can be validated, verified, reinforced, calibrated, or otherwise updated based on newly received, up-to-date data; historical data or be updated based on any other suitable data. However, determining personalized food parameters can be performed in any suitable manner.

2.4 Presenting Personalized Food Parameters

Block S140 recites: presenting the personalized food parameters to at least one of the user and a subject matter expert, which can function to enable selection of personalized food-related options and/or other suitable food parameters for facilitating fulfillment (e.g., food-related purchasing fulfillment such as for food items corresponding to recipe items for one or more meal options; food delivery fulfillment such as for delivering selected meal options, associated food items, and/or other suitable personalized food parameters; etc.), delivering personalized content (e.g., personalized recipes satisfying user food-related preferences; food-related goal analytics; health recommendations; etc.); updating of food-related models (e.g., where user selections and/or other suitable feedback for presented personalized food parameters can be used as inputs in updating food personalization models and/or other suitable models, such as through a food personalization feedback loop; etc.) and/or other suitable purposes.

Personalized food parameters are preferably presented at a user interface (e.g., presented at a mobile application executing on a user mobile device, etc.) and/or SME interface (e.g., for collecting dietary inputs regarding the determined personalized food parameters; regarding the personalized food parameters selected by a user; etc.), but can be presented at any suitable computing device and/or components.

Presenting food parameters can be performed at a predetermined time period (e.g., for notifications transmitted at predetermined times, etc.), in response to, concurrently with, serially with, and/or in any suitable temporal relation to a trigger condition (e.g., determination of the personalized food parameters, a user selection of a food browsing option at a user interface, etc.), and/or at any suitable time and frequency.

In a variation, Block S140 can include modifying one or more presentation parameters (e.g., for encouraging user selections of personalized food parameter options suited to achieving user food-related goals, etc.) including any one or more of: textual parameters (e.g., meal option descriptions; recipe descriptions; font; color; placement; etc.), graphical parameters (e.g., images, video, augmented reality, virtual reality, other media, etc.), audio parameters, and/or any other suitable parameters.

In another variation, Block S140 can include generating a recipe using the personalized food parameters (e.g., according to a vector representation of the personalized food parameters, using a recipe generation model that accepts a vector or other suitable food parameterization as an input, etc.).

However, presenting personalized food parameters can be performed in any suitable manner.

2.5 Updating Food-Related Components

The method 100 can additionally or alternatively include Block S150, which recites: updating a food personalization model (and/or other suitable food-related model), other components associated with determining personalized food parameters, and/or any other suitable components associated with the method 100. Block S150 can function to update food-related components based on additional data (e.g., newly collected user food-related preferences, dietary inputs from SME, user inputs and/or other suitable interactions with interfaces; etc.) to improve the food-related personalization. For example, Block S150 can include presenting a set of alternative meal options to a user; receiving, from the user, a selection of a meal option from the set of alternative meal options; updating a food personalization model (e.g., for determining future alternative meal options for the user and/or other suitable users such as users with shared user food-related preferences, etc.), user food-related preferences for the user, and/or other suitable components based on the user selection of the meal option and/or associated data (e.g., associated ranking displayed during presentation of the alternative meal options; associated recipe data; associated dietary inputs regarding the selected meal option and/or the alternative meal options; etc.); and repeating the processes for applying a reinforcement learning mechanism (e.g., through observing user outcomes, adjusting parameters such as those associated with a food personalization model; for maximizing a joint utility across user satisfaction and/or food-related goal outcomes; etc.).

In a variation, Block S150 can include updating based on supplementary data (e.g., describing progress towards user food-related goals; indicating satisfaction of other user food-related preferences; describing user satisfaction; supplementing food parameter information such as nutrition facts; mapping supplementary data to progress towards goals; etc.) including any one or more of: supplementary sensor data (e.g., biometric devices, health tracker data such as activity trackers, connected scales, etc.), food device data (e.g., cooking device data describing consumed food items, etc.), media data (e.g., images, videos, other media, capturing consumed food items, capturing purchased food items, capturing desired food items, etc.), medical data (e.g., medical history, care provider visits, etc.), survey data (e.g., survey responses from users, SMEs, etc.), and/or any other suitable supplementary data. In another variation, Block S150 can include facilitating preparation of a food item (e.g., according to a recipe). Such a variation can include generating control instructions for a connected cooking device (e.g., a smart oven, a smart immersion circulator, etc.), controlling a connected device (e.g., using a set of control instructions thus generated), and/or performing any other suitable action.

Block S150 is preferably performed at a remote computing system (e.g., for training, storing, retrieving, executing, and/or otherwise applying food-related models, etc.) wirelessly communicable with one or more user devices, SME devices, and/or other suitable computing devices, such as in an inventive distribution of functionality across a network for improving food-related personalization; additionally or alternatively, Block S150 can be performed with any suitable components (e.g., of the system 200). However, Block S150 can be performed in any suitable manner.

2.6 Specific Examples

In a specific example, the method includes determining food-related preferences associated with a plurality of users, including: collecting selections from each of the plurality of users at a user interface, and explicitly determining food-related preferences based on the selections, inferring food-related preferences of each of the plurality of users based on user actions in relation to the user interface, and mapping food-related preferences to food parameters represented in a recipe vector space to generate a user food preferences database (e.g., Block S110); collecting dietary inputs from a subject matter expert (SME) at an SME interface associated with the user food preferences database (e.g., Block S120); determining personalized food parameters for the user based on the user food-related preferences and the dietary inputs (e.g., in accordance with a variation of Block S130); generating a recipe based on the personalized food parameters (e.g., in accordance with a variation of Block 140); and automatically facilitating preparation of the recipe by the user (e.g., in accordance with a variation Block S150).

In a related specific example, the method includes mapping food-related preferences to food parameters as described above wherein mapping includes providing the food-related preferences to a trained neural network model as input vectors, wherein the trained neural network model comprises a plurality of neuronal layers that each transform the input vector received from the preceding neuronal layer of the plurality of neuronal layers into an intermediate vector provided as an input vector to a subsequent neuronal layer, wherein the food parameters define a vector in the recipe vector space equivalent to an intermediate vector transformed by one of the plurality of neuronal layers.

In another related specific example, the method includes explicitly determining food-related preferences as described above, wherein it includes defining an initial preference vector, associated with each of the plurality of users user, in the recipe vector space, wherein the initial preference vector defines a first coverage of the recipe vector space; generating a minimal set of candidate recipes in the recipe vector space, based on the first coverage, wherein the minimal set of candidate recipes defines a second coverage of the recipe vector space; collecting selections from the minimal set of candidate recipes; and updating the initial preference vector to generate an updated preference vector associated with each of the plurality of users. The first and second coverage can be overlapping, non-overlapping, complete in combination (e.g., complementary), and/or have any other suitable relative or absolute coverage of the recipe vector space.

In another specific example, the method for improving food-related personalized for a user includes: determining food-related preferences associated with a plurality of users to generate a user food preferences database; collecting dietary inputs from a subject matter expert (SME) at an SME interface associated with the user food preferences database; determining personalized food parameters for the user based on the user food-related preferences and the dietary inputs; receiving a score associated with the personalized food parameters from the user at a user interface; and updating the user food preferences database based on the score.

Although omitted for conciseness, the preferred embodiments include every combination and permutation of the various system components and the various method processes, including any variations, examples, and specific examples, where the method processes can be performed in any suitable order, sequentially or concurrently.

The system and method and variations thereof can be embodied and/or implemented at least in part as a machine configured to receive a computer-readable medium storing computer-readable instructions. The instructions are preferably executed by computer-executable components preferably integrated with the system.

The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

As a person skilled in the art will recognize from the previous detailed description and from the figures and claims, modifications and changes can be made to the preferred embodiments of the invention without departing from the scope of this invention defined in the following claims.

We claim:

1. A method for improving food-related personalized for a user comprising:
    determining food-related preferences associated with a plurality of users, comprising:
        collecting selections from each of the plurality of users at a user interface, and explicitly determining food-related preferences based on the selections,
        inferring food-related preferences of each of the plurality of users based on user actions in relation to the user interface, and
        mapping food-related preferences to food parameters represented in a recipe vector space to generate a user food preferences database, wherein mapping food-related preferences to food parameters comprises:
            providing the food-related preferences to a trained neural network model as input vectors, wherein the trained neural network model comprises a plurality of neuronal layers that each transform the input vector received from the preceding neuronal layer of the plurality of neuronal layers into an intermediate vector provided as an input vector to a subsequent neuronal layer,
            wherein the food parameters define a vector in the recipe vector space equivalent to an intermediate vector transformed by one of the plurality of neuronal layers;
    collecting dietary inputs from a subject matter expert (SME) at an SME interface associated with the user food preferences database;
    determining personalized food parameters for the user based on the user food-related preferences and the dietary inputs;
    generating a recipe based on the personalized food parameters; and
    automatically facilitating preparation of the recipe by the user comprising controlling a connected cooking appliance based on the personalized food parameters.

2. The method of claim 1, wherein the food-related preferences comprise at least one of health goals, taste preferences, and dietary restrictions of each of the plurality of users.

3. The method of claim 2, wherein determining the food-related preferences comprises applying natural language processing to medical records associated with at least one user to extract health goals associated with the at least one user.

4. The method of claim 1, wherein determining food-related preferences further comprises collecting an exogenous signal from a third-party entity.

5. The method of claim 4, wherein the exogenous signal comprises social media content, and determining food-related preferences of at least one user of the plurality of users comprises inferring food-related preferences based on social media content sampled from a social media account associated with the at least one user.

6. The method of claim 4, wherein the exogenous signal comprises an output of natural language processing of electronic messages exchanged by the user.

7. The method of claim 1, wherein inferring food-related preferences based on user actions comprises inferring food-related preferences of at least one user of the plurality of users from a historical record of food item usage rate by that user.

8. The method of claim 1, wherein explicitly determining food-related preferences based on the selections comprises:
    defining an initial preference vector, associated with each of the plurality of users, in the recipe vector space, wherein the initial preference vector defines a first coverage of the recipe vector space;
    generating a minimal set of candidate recipes in the recipe vector space, based on the first coverage, wherein the minimal set of candidate recipes defines a second coverage of the recipe vector space;
    collecting selections from the minimal set of candidate recipes; and updating the initial preference vector to generate an updated preference vector associated with each of the plurality of users.

9. The method of claim 8, wherein the second coverage is complementary to the first coverage of the recipe vector space.

10. The method of claim 1, wherein collecting dietary inputs comprises collecting labeled training data for a machine-learning based dietary model, wherein the labeled training data comprises dietary data represented in the recipe vector space, and wherein dietary data are labeled according to the dimensions of the recipe vector space.

11. The method of claim 1, wherein collecting dietary inputs comprises dividing the plurality of users into subgroups of users based on shared user food-related preferences according to a series of computer-implemented dietary rules, and wherein determining personalized food parameters for the user is based on the shared food-related preferences of the user's subgroup.

12. The method of claim 1, wherein the SME comprises a trained machine-learning based dietary model.

13. The method of claim 1, wherein the personalized food parameters comprise a set of recipe vectors represented in the recipe vector space, wherein the food-related preferences define a vector magnitude constraint, and wherein each of the recipe vectors in the set of recipe vectors defines a magnitude less than the vector magnitude constraint.

* * * * *